United States Patent [19]

Shankar et al.

[11] Patent Number: 5,491,155

[45] Date of Patent: Feb. 13, 1996

[54] SUBSTITUTED THIADIAZOLES, COMPOSITIONS CONTAINING THEM AND THEIR USE AS ANTIMICROBIAL AND MARINE ANTIFOULING AGENTS

[75] Inventors: Ravi B. Shankar; R. Garth Pews; Duane R. Romer, all of Midland, Mich.

[73] Assignee: The Dow Chemical Company, Midland, Mich.

[21] Appl. No.: 360,497

[22] Filed: Dec. 21, 1994

[51] Int. Cl.⁶ .................. A61K 31/41; A01N 43/832; C07D 285/10
[52] U.S. Cl. ................... 514/362; 504/261; 548/135
[58] Field of Search ................... 548/135; 514/362

[56] References Cited

U.S. PATENT DOCUMENTS

| | | | |
|---|---|---|---|
| 3,753,999 | 8/1973 | Tempel et al. | 260/306.6 |
| 3,888,869 | 6/1975 | Pews et al. | 260/302 |
| 4,094,880 | 6/1978 | Goralski et al. | 260/302 |

FOREIGN PATENT DOCUMENTS 0433616  10/1990  European Pat. Off. .

*Primary Examiner*—Johann Richter
*Assistant Examiner*—Laura L. Stockton
*Attorney, Agent, or Firm*—S. Preston Jones; James M. Pelton

[57] ABSTRACT

Substituted thiadiazoles which correspond to the formula:

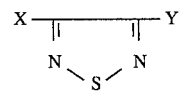

wherein X and Y each independently represents —Br, —Cl, —OCH$_3$, —SCN, —OCH$_2$SCN, —SCH$_2$SCN, —OCH$_2$CH$_2$SCN or —SCH$_2$CH$_2$SCN, provided that at least one of X or Y represents —SCN, —OCH$_2$SCN, —SCH$_2$SCN, —OCH$_2$CH$_2$SCN or —SCH$_2$CH$_2$SCN are disclosed.

These compounds have been found to exhibit antimicrobial and marine antifouling activity in industrial and commercial applications and compositions containing these compounds are so employed.

45 Claims, No Drawings

SUBSTITUTED THIADIAZOLES, COMPOSITIONS CONTAINING THEM AND THEIR USE AS ANTIMICROBIAL AND MARINE ANTIFOULING AGENTS

FIELD OF THE INVENTION

The present invention is directed to novel substituted thiadiazole compounds, compositions containing said compounds and the use of these compositions as antimicrobial and marine antifouling agents.

BACKGROUND OF THE INVENTION

EP 0 433 616 A2 discloses antimicrobials for the control of bacteria and fungi and teaches the preparation of compounds of the formula:

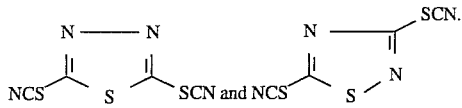

U.S. Pat. No. 4,094,880 discloses antimicrobials for the control of bacteria and fungi and the preparation and the antimicrobial use of 2,5-bis(chloromethylthio)-1,3,4-thiadiazole and its isomer 3,5-bis(chloromethylthio)-1,2,4-thiadiazole of compounds of the formula:

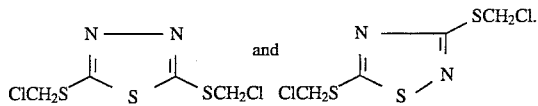

U.S. Pat. No. 3,888,869 discloses the preparation of compounds of the formula:

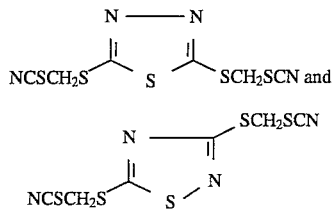

which compounds are useful as antimicrobials.

While the above compounds are somewhat active, it is still desirable to identify and/or discover new antimicrobial and/or marine antifoulant agents. Many of the known antimicrobial/marine antifoulant agents have been found to be of minimal value for several reasons; these include, but are not limited to, the problem created by microbe strains developing resistance to known agents, the occurrence of undesirable interactions of certain known agents with the medium or product in which the agent is used; and the high toxicity of certain known agents to certain non-target organisms, including mammals.

SUMMARY OF THE INVENTION

The present invention is directed to compounds corresponding to the formula:

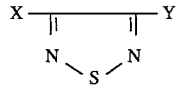

wherein X and Y each independently represents —Br, —Cl, —OCH₃, —SCN, —OCH₂SCN, —SCH₂SCN, —OCH₂CH₂SCN or —SCH₂CH₂SCN, provided that at least one of X or Y represents —SCN, —OCH₂SCN, —SCH₂SCN, —OCH₂CH₂SCN or —SCH₂CH₂SCN.

The present invention is also directed to antimicrobial compositions comprising an inert diluent and an antimicrobially-effective amount of a compound corresponding to Formula 1.

The present invention is further directed to a method for inhibiting microorganisms in a microbial habitat comprising contacting said microbial habitat with an antimicrobially-effective amount of a compound corresponding to Formula 1.

The antimicrobial compositions of the present invention can also be employed to treat surfaces exposed to a marine environment in which marine organisms grow to prevent the growth of said marine organisms on said surfaces.

The preferred compounds of the present invention include those wherein X represents —Cl or —SCN when Y is —SCN; those wherein X represents —Cl or —SCH₂SCN when Y is —SCH₂SCN and those wherein X represents —Cl or —SCH₂CH₂SCN when Y is —SCH₂CH₂SCN.

DETAILED DESCRIPTION OF THE INVENTION

In the present specification and claims, the term "alkali metal" is employed to designate sodium, potassium, lithium or cesium.

In the present specification and claims, the term "halo" is employed to designate bromo, chloro, fluoro or iodo.

In the following process schematic formulas, certain specific alkali metals, halo groups, specific solvents and the like are set forth. These representations are only presented for convenience and are not to be considered as an indication that these specific representations are the only groups or materials which can be employed. The reactions as set forth below and in the specific examples can all be carried out at room temperature in the presence of conventional reaction mediums, such as for example, a 70% ethanol/30% water mixture.

The halothiocyanato-1,2,5-thiadiazole compounds of the present invention, wherein X represents halo and Y represents —SCN, may be prepared by first reacting a 3,4-dihalo-1,2,5-thiadiazole such as, for example, 3,4-dichloro-1,2,5-thiadiazole, with an alkali metal sulfide, such as sodium sulfide, to produce a (halomercapto)-1,2,5-thiadiazole: alkali metal salt, such as (4-chloro-3-mercapto)-1,2,5-thiadiazole: sodium salt. The general scheme for this first reaction step is as follows:

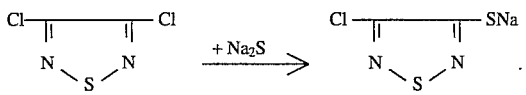

The above (halomercapto)-1,2,5-thiadiazole: alkali metal salt product is then reacted with a cyanogen halide, such as cyanogen bromide to prepare the desired halothiocyanato-1,2,5-thiadiazole product. The reaction consumes the reactants in the ratio of one mole equivalent of the cyanogen halide per mole of the (halomercapto)-1,2,5-thiadiazole: alkali metal salt reactant to prepare the desired halothiocyanato-1,2,5-thiadiazole product and thus equimolar amounts of the reactants are employed.

The general scheme for this second reaction step is as follows:

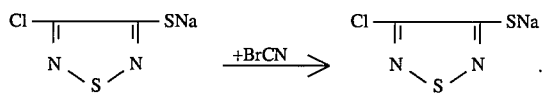

The bis(thiocyanato)-1,2,5-thiadiazole compound of the present invention, wherein X and Y both represent —SCN, may be prepared by first reacting an alkali metal sulfide, such as sodium sulfide, with a 4,5-dihalo-1,2,5-thiadiazole, such as 3,4-dichloro-1,2,5-thiadiazole, to produce a bis(mercapto)-1,2,5-thiadiazole: di(alkali metal) salt, such as the bis(mercapto)-1,2,5-thiadiazole: disodium salt. The general scheme for this first reaction step is as follows:

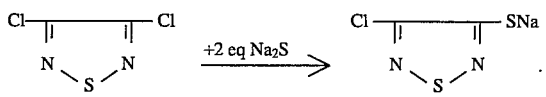

The desired bis(thiocyanato)-1,2,5-thiadiazole is then prepared by reacting the thus prepared bis(mercapto)-1,2,5-thiadiazole: di(alkali metal) salt with a cyanogen halide, such as cyanogen bromide. Two mole equivalents of the cyanogen halide are used per mole of the bis(mercapto)-1,2,5-thiadiazole, di(alkali metal) salt to prepare the bis(thiocyanato)-1,2,5-thiadiazole.

The general scheme for this second reaction step is as follows:

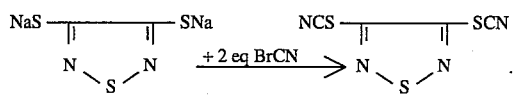

The halothiomethyl(or ethyl)thiocyanato-1,2,5-thiadiazole compounds of the present invention, wherein, for example, X represents —Cl or —Br and Y represents —SCH$_2$SCN or —SCH$_2$CH$_2$SCN, may be prepared by first preparing a (halomercapto)-1,2,5-thiadiazole, alkali metal salt, as described hereinabove. The halothiomethylthiocyanato-1,2,5-thiadiazole is then prepared by reacting the (halomercapto)-1,2,5-thiadiazole, alkali metal salt with a halomethyl(or ethyl)thiocyanate, such as chloromethyl-thiocyanate or chloroethylthiocyanate. One mole equivalent of the halomethyl(or ethyl)thiocyanate is used per mole of (halomercapto)-1,2,5-thiadiazole: alkali metal salt to prepare the halothiomethyl(or ethyl)thiocyanato-1,2,5-thiadiazole.

The general reaction scheme is as follows:

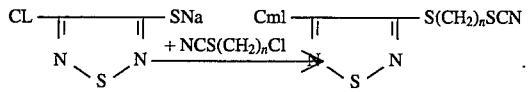

wherein n is 1 or 2.

The bis(thiomethyl(or thioethyl)thiocyanato-1,2,5-thiadiazole compounds of the present invention, wherein, for example, X and Y each represent —SCH$_2$SCN or —SCH$_2$CH$_2$SCN, may be prepared by reacting a halomethyl(or ethyl)thiocyanate, such as chloromethylthiocyanate or chloroethylthiocyanate with a bis(mercapto)-1,2,5-thiadiazole: alkali metal salt (prepared as described hereinabove). Two mole equivalents of the halomethyl(or ethyl)thiocyanate is used per mole of the bis(mercapto)-1,2,5-thiadiazole: alkali metal salt to prepare the desired bis(thiomethyl(or thioethyl)-thiocyanato-1,2,5-thiadiazole.

The general reaction scheme is as follows:

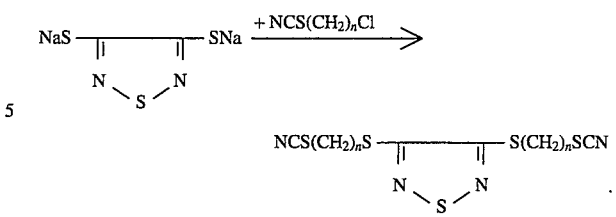

wherein n is 1 or 2.

Preferably, the above reactions are carried out in an inert solvent such as dimethylformamide, methanol, ethanol, acetonitrile, acetone, or pyridine. Preferably, the reactions are carried out at 0° C. under an ambient pressure of inert gas. Subsequent to the addition of the appropriate reaction materials, the reaction mixture is allowed to stir at a temperature of between about 25° C. to about 60° C. for a period of between about 2 to about 24 hours in order to increase the reaction rate and promote extinction of the limiting reagent. Final work-up of the reaction mixture then provides the desired final product.

The thiadiazole compounds of the present invention, wherein X represents —SCN and Y represents —SCH$_2$SCN or —SCH$_2$CH$_2$SCN, may be prepared by first reacting a 4-halo-3-thiomethyl(or ethyl)thiocyanato-1,2,5-thiadiazole, as prepared hereinbefore, an alkali metal sulfide, such as sodium sulfide, followed by reacting the thus formed 4-mercapto-3-thiomethyl(or ethyl)thiocyanato-1,2,5-thiadiazole: alkali metal salt with a cyanogen halide, such as cyanogen bromide to form the desired 3-thiocyanato-4-thiomethyl(or ethyl)thiocyanato-1,2,5-thiadiazole. In the above reactions, equimolar amounts of the reactants are normally employed. The general scheme for this reaction step is as follows:

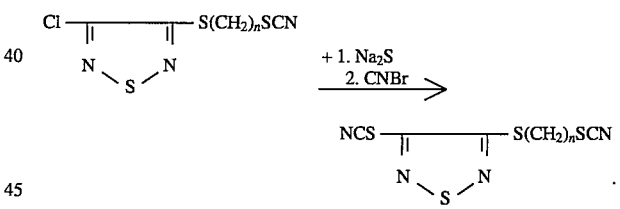

The thiadiazole compounds of the present invention, wherein X represents —SCH$_2$SCN and Y represents —SCH$_2$CH$_2$SCN, may be prepared by first reacting a 3-halo-4-mercapto-1,2,5-thiadiazole: alkali metal salt, as prepared hereinbefore, with a dihaloethane such as 1-bromo-2-chloroethane to produce a 4-halo-3-halothioethyl-1,2,5-thiadiazole such as 4-chloro-3-chlorothioethyl-1,2,5-thiadiazole. The general scheme for this reaction step is as follows:

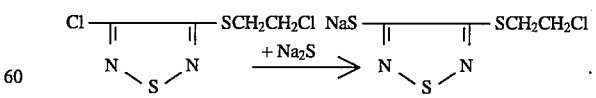

The thus formed 4-halo-3-halothioethyl-1,2,5-thiadiazole is then reacted with an alkali metal sulfide, such as sodium sulfide, to produce the corresponding alkali metal salt, such as 4-mercapto-3-halothioethyl-1,2,5-thiadiazole: sodium salt. The general scheme for this reaction step is as follows:

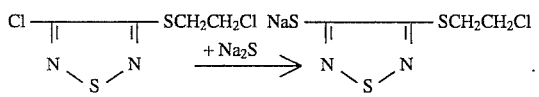

This product can, without separation and purification, be reacted with a halomethylthiocyanate, such as chloromethylthiocyanate to form a 3-halothioethyl-4-thiomethyl-thiocyanato-1,2,5-thiadiazole, such as 3-chlorothioethyl-4-thiomethyl-thiocyanato-1,2,5-thiadiazole. One mole equivalent of the halomethylthiocyanate reactant is used per mole of the 4-mercapto-3-halothioethyl-1,2,5-thiadiazole: alkali metal salt and such equimolar amounts of the reactants are normally employed. The general scheme for this reaction step is as follows:

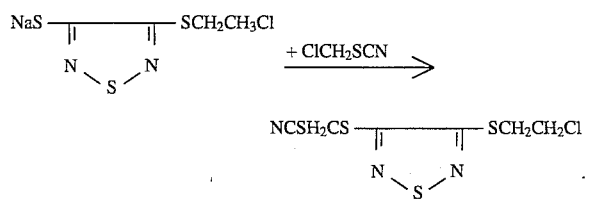

The above 3-halothioethyl-4-thiomethyl-thiocyanato-1,2,5-thiadiazole product is dissolved in a solvent such as acetone containing an alkali metal thiocyanate such as potassium thiocyanate and refluxed for a period of about 16 hours. The reaction mixture is filtered, and concentrated under reduced pressure and the residue treated by conventional procedures such as, chromatography over silica gel using hexane/ethyl acetate as eluent, to recover the desired 3-thioethylthiocyanato-4-thiomethyl-thiocyanatomethyl-1,2,5-thiadiazole. The reaction consumes the reactants in the ratio of one mole equivalent of the alkali metal thiocyanate per mole of the thiadiazole reactant and such equimolar amounts of the reactants are normally employed. However to ensure completion of the reaction, a slight excess, about 1.0–1.25 equivalents, of alkali metal thiocyanate is usually provided. The general scheme for this reaction step is as follows:

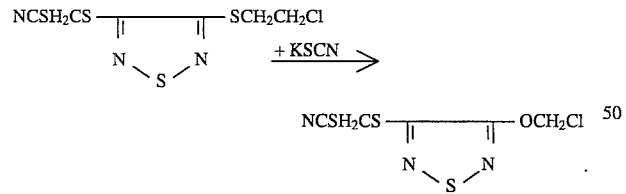

The halothiocyanatomethyloxo-1,2,5-thiadiazole compounds of the present invention, wherein, for example, X represents —Cl or —Br and Y represents —OCH$_2$SCN, may be prepared by first irradiating a solution of 4-halo-3-methoxy-1,2,5-thiadiazole such as 4-chloro-3-methoxy-1,2,5-thiadiazole in carbon tetrachloride with a sunlamp while adding a solution of sulfuryl chloride in carbon tetrachloride. Upon completion of the reaction, the reaction mixture is washed with aqueous sodium bicarbonate and concentrated under reduced pressure to yield 4-chloro-3-halomethoxy-1,2,5-thiadiazole. The general scheme for this first reaction step is as follows:

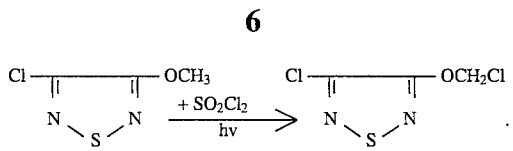

The above 4-chloro-3-halomethoxy-1,2,5-thiadiazole product is dissolved in a solvent such as acetone containing an alkali metal thiocyanate such as potassium thiocyanate and refluxed for a period of about hours. The reaction mixture is filtered, and concentrated under reduced pressure and the residue treated by conventional procedures such as, chromatography over silica gel using hexane/ethyl acetate as eluent, to recover the desired halothiocyanatomethyloxo-1,2,5-thiadiazole. The reaction consumes the reactants in the ratio of one mole equivalent of the alkali metal thiocyanate per mole of the thiadiazole reactant and such equimolar amounts of the reactants are normally employed. However to ensure completion of the reaction, a slight excess, about 1.0–1.25 equivalents, of alkali metal thiocyanate is usually provided.

The general scheme for this second reaction step is as follows:

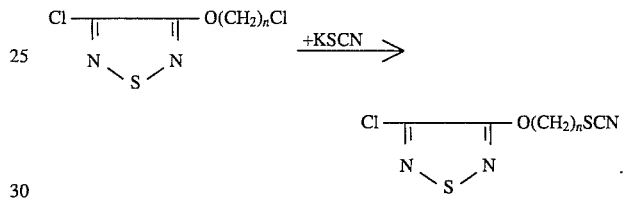

The bis(thiomethyloxothiocyanato)-1,2,5-thiadiazole compounds of the present invention, wherein X and Y both represent —O(CH$_2$)$_n$SCN and n is 1 or 2, may be prepared by first irradiating a solution of a bis(methoxy)-1,2,5-thiadiazole in carbon tetrachloride with a sunlamp while adding a solution of sulfuryl chloride in carbon tetrachloride. The reaction mixture is washed with aqueous sodium bicarbonate and concentrated under reduced pressure to yield bis-(chloromethoxy)-1,2,5-thiadiazole. The general scheme for this first reaction step is as follows:

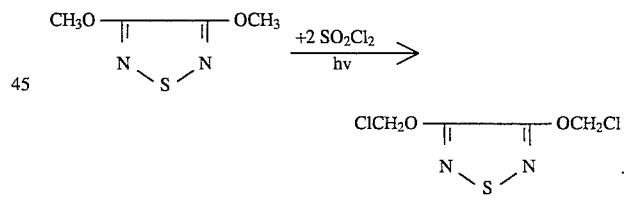

The above bis(chloromethoxy)-1,2,5-thiadiazole is dissolved in a solvent such as acetone containing an alkali metal thiocyanate such as potassium thiocyanate and refluxed for a period of about 16 hours. The reaction mixture is filtered, and concentrated under reduced pressure and the residue treated by conventional procedures such as, chromatography over silica gel using hexane/ethyl acetate as eluent, to recover the desired bis(thiomethyloxothiocyanato)-1,2,5-thiadiazole compound. The reaction consumes the reactants in the ratio of two mole equivalents of the alkali metal thiocyanate per mole of the thiadiazole reactant and such amounts of the reactants are normally employed. However to ensure completion of the reaction, a slight excess, about 1.2–1.25 equivalents, of alkali metal thiocyanate is usually provided.

The general reaction scheme for this reaction is as follows:

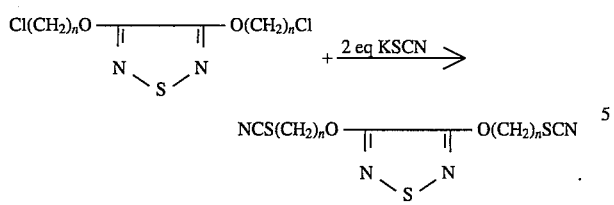

The 4-methoxy-3-thiocyanatomethyloxo-1,2,5-thiadiazole compound of the present invention, i.e., wherein X represents —$OCH_3$ and Y represents —$OCH_2SCN$ may be prepared by first irradiating a solution of a bis(methoxy)-1,2,5-thiadiazole in carbon tetrachloride with a sunlamp while adding a solution of sulfuryl chloride in carbon tetrachloride. Upon completion of the reaction, the reaction mixture is washed with aqueous sodium bicarbonate and concentrated under reduced pressure to yield 4-methoxy-3-halomethoxy-1,2,5-thiadiazole. This product is then dissolved in a solvent such as acetone containing an alkali metal thiocyanate such as potassium thiocyanate and refluxed for a period of about 16 hours. The reaction mixture is filtered, and concentrated under reduced pressure and the residue treated by conventional procedures such as, chromatography over silica gel using hexane/ethyl acetate as eluent, to recover the desired 4-methoxy-3-thiocyanatomethyloxo-1,2,5-thiadiazole. The reaction consumes the reactants in the ratio of one mole equivalent of the alkali metal thiocyanate per mole of the thiadiazole reactant and such equimolar amounts of the reactants are normally employed. However to ensure completion of the reaction, a slight excess, about 1.0–1.25 equivalents, of alkali metal thiocyanate is usually provided. The general scheme for these reaction steps are as follows:

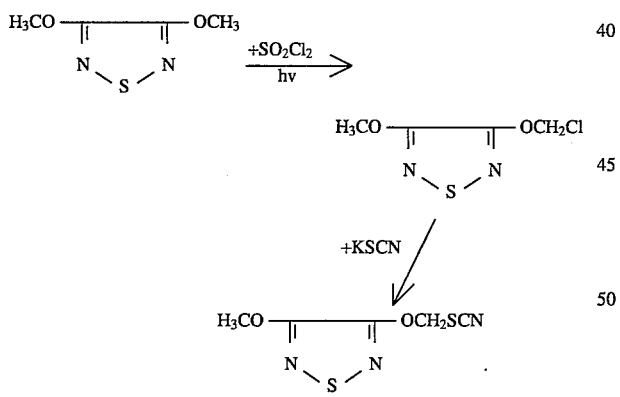

The 4-methoxy-3-thiocyanatoethyloxo-1,2,5-thiadiazole compound of the present invention, i.e., wherein X represents —$OCH_3$ and Y represents —$OCH_2CH_2SCN$ may be prepared by treating 4-chloro-3-methoxy-1,2,5-thiadiazole, prepared as set forth hereinbefore, with an alkali metal hydroxide, such as sodium hydroxide, to prepare the corresponding 4-hydroxy-3-methoxy-1,2,5-thiadiazole which is then reacted with a haloethylthiocyanate, such as chloroethylthiocyanate to give the desired 4-methoxy-3-thiocyanatoethyloxo-1,2,5-thiadiazole product. The general reaction scheme is as follows:

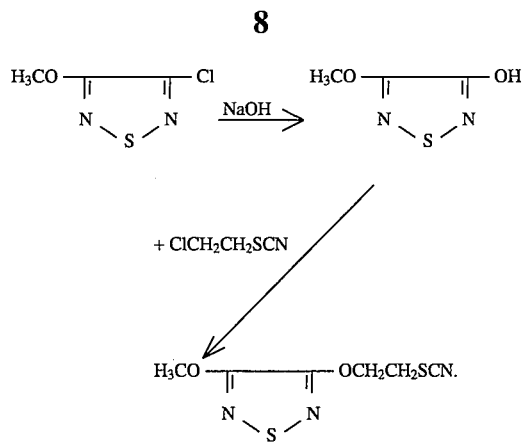

The 3-thiocyanatoethyloxo-4-thiocyanato-methyloxo-1,2,5-thiadiazole compound of the present invention, i.e., wherein X represents —$OCH_2SCN$ and Y represents —$OCH_2CH_2SCN$ may be prepared by treating a 4-halo-3-thiocyanatomethyloxo-1,2,5-thiadiazole, such as 4-chloro-3-thiocyanatomethyloxo-1,2,5-thiadiazole, prepared as set forth hereinbefore, with an alkali metal hydroxide, such as sodium hydroxide, to prepare the corresponding 4-hydroxy-3-thiocyanato-methyloxo-1,2,5-thiadiazole which is then reacted with a haloethylthiocyanate, such as chloroethylthiocyanate to give the desired 3-thiocyanatoethyloxo-4-thiocyanato-methyloxo-1,2,5-thiadiazole product. The general reaction scheme is as follows:

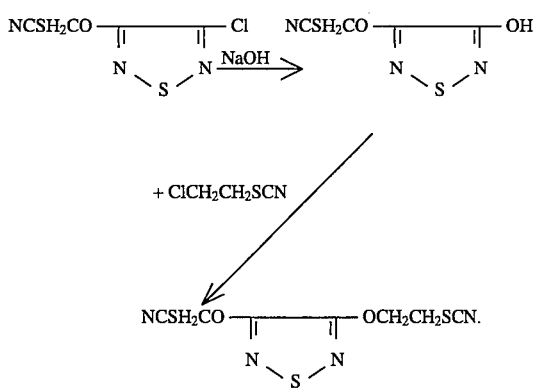

The 3-methoxy-4-thiocyanato-1,2,5-thiadiazole compound of the present invention, wherein, X represents —$OCH_3$ and Y represents —SCN, may be prepared by reacting a 4-halo-3-methoxy-1,2,5-thiadiazole such as 4-chloro-3-methoxy-1,2,5-thiadiazole, prepared as set forth hereinbefore, with an alkali metal sulfide, such as sodium sulfide followed by reacting the thus formed 3-methoxy-4-mercapto-1,2,5-thiadiazole; alkali metal salt with a cyanogen halide, such as cyanogen bromide to form the desired 3-methoxy-4-thiocyanato-1,2,5-thiadiazole. The general scheme for this reaction is as follows:

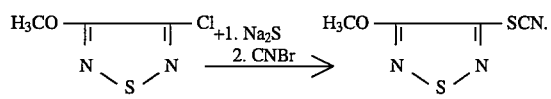

The 3-methoxy-4-thiomethyl(or ethyl)-thiocyanato-1,2,5-thiadiazole compounds of the present invention, wherein, for example, X represents —$OCH_3$ represents —$SCH_2SCN$ or —$SCH_2CH_2SCN$, may be prepared by reacting at room temperature in dimethylformamide a 3-methoxy-4-mercapto-1,2,5-thiadiazole; alkali metal salt, such as 3-methoxy-4-mercapto-1,2,5-thiadiazole; sodium salt, prepared as set forth hereinbefore, with a halomethyl(or ethyl)thiocyanate, such as chloromethyl-thiocyanate or chloroethylthiocyanate. One mole equivalent of the halomethyl(or ethyl)thiocyanate is used per mole of the 3-methoxy-4-mercapto)-1,2,5-thiadiazole: alkali metal salt to prepare the 3-methoxy-4-thiomethyl(or ethyl)thiocyanato-1,2,5-thiadiazole.

The general reaction scheme is as follows:

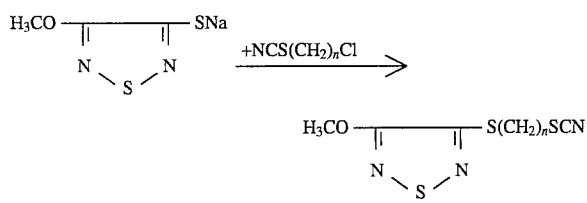

wherein n is 1 or 2.

The 3-thiocyanatomethyloxo-4-thiocyanato--1,2,5-thiadiazole compound of the present invention, wherein, for example, X represents —OCH$_2$SCN and Y represents —SCN, may be prepared by reacting a 4-chloro-3-halomethoxy-1,2,5-thiadiazole such as 4-chloro-3-chloromethoxy-1,2,5-thiadiazole, prepared as set forth hereinbefore, with 2 equivalents of an alkali metal sulfide, such as sodium sulfide followed by reacting the thus formed 4-mercaptomethoxy-3-mercapto-1,2,5-thiadiazole, dialkali metal salt with 2 equivalents of a cyanogen halide, such as cyanogen bromide to form the desired 3-thiocyanatomethyloxo-4-thiocyanato-1,2,5-thiadiazole. The general scheme for this reaction is as follows:

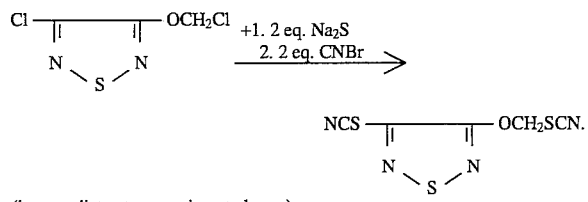

(intermediate structure is not shown)

The 3-thiocyanato-4-thiocyanatoethyloxo-1,2,5-thiadiazole compound of the present invention, wherein, for example, X represents —OCH$_2$CH$_2$SCN and Y represents —SCN, may be prepared by first reacting a 3,4-dihalo-1,2,5-thiadiazole, such as 3,4-dichloro-1,2,5-thiadiazole with an alkali metal hydroxide, such as sodium hydroxide and the resulting 3-chloro-4-hydroxy-1,2,5-thiadiazole: sodium salt is then reacted at room temperature in dimethylformamide with chloroethyltosylate(Tso-CH$_2$CH$_2$Cl). The thus formed 3-chloro-4-chloroethyloxy-1,2,5-thiadiazole is then reacted with an alkali metal sulfide, such as sodium sulfide followed by reacting the thus formed 3-mercapto-4-chloroethyloxy-1,2,5-thiadiazole: alkali metal salt with 2 equivalents of a cyanogen halide, such as cyanogen bromide to form the desired 3-thiocyanato-4-thiocyanatoethyloxo-1,2,5-thiadiazole. The general scheme for this reaction is as follows:

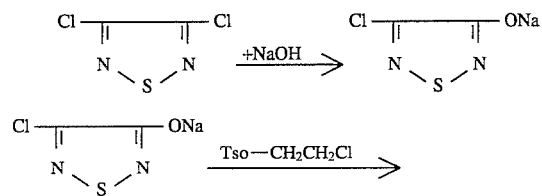

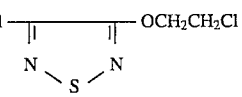

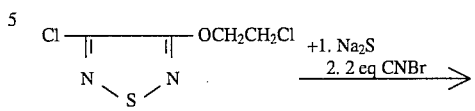

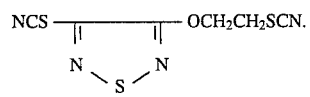

(intermediate structure is not shown)

The 3-thiomethyl(or ethyl)cyanato-4-thiocyanatomethyloxo-1,2,5-thiadiazole compound of the present invention, wherein, for example, X represents —OCH$_2$SCN and Y represents —S(CH$_2$)$_n$SCN wherein n is as defined hereinbefore, may be prepared by irradiating a solution of 3-methoxy-4-thiomethyl(or ethyl)thiocyanato-1,2,5-thiadiazole, prepared as described hereinbefore, in a solvent such as carbon tetrachloride with a sunlamp while adding a solution of a sulfuryl halide such as sulfuryl chloride in a solvent such as carbon tetrachloride. The thus formed 3-halomethoxy-4-thiomethyl(or ethyl)thiocyanato-t,2,5-thiadiazole product is dissolved in a solvent such as acetone containing an alkali metal thiocyanate such as potassium thiocyanate and refluxed for a period of about 16 hours. The reaction mixture is filtered, and concentrated under reduced pressure and the residue treated by conventional procedures such as, chromatography over silica gel using hexane/ethyl acetate as eluent, to recover the desired above-indicated compound. The reaction consumes the reactants in the ratio of one mole equivalent of the alkali metal thiocyanate per mole of the thiadiazole reactant and such equimolar amounts of the reactants are normally employed. However to ensure completion of the reaction, a slight excess, about 1.0–1.25 equivalents, of alkali metal thiocyanate is usually provided. The general scheme for this reaction is as follows:

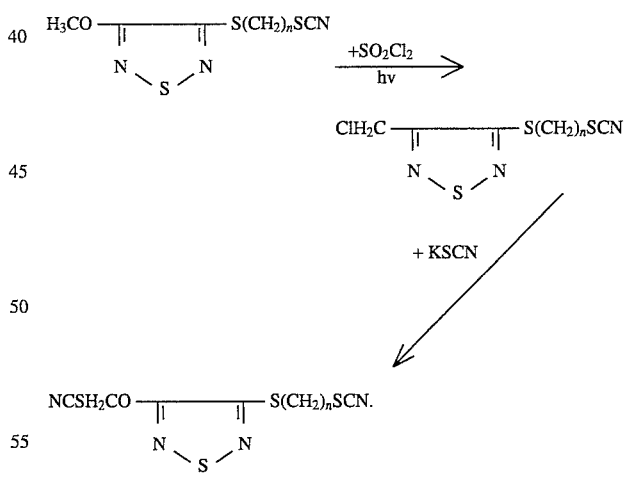

The 3-thiomethylcyanato-4-thiocyanatoethyloxo-1,2,5-thiadiazole compound of the present invention, wherein, for example, X represents —OCH$_2$CH$_2$SCN and Y represents —SCH$_2$SCN, may be prepared by first reacting a 4-halo-3-thiomethylcyanato-1,2,5-thiadiazole, such as 4-chloro-3-thiomethyl-cyanato-1,2,5-thiadiazole, prepared as described hereinbefore, with an alkali metal hydroxide, such as sodium hydroxide and the thus formed 4-hydroxy-3-thiomethylcyanato-1,2,5-thiadiazole: sodium salt is then reacted at room temperature in dimethylformamide with a haloethylthiocyanate, such as chloroethylthiocyanate to prepare the desired -thiomethylcyanato-4-thiocyanato-ethyloxo-1,2,5-thiadiazole. The general scheme for this reaction is as follows:

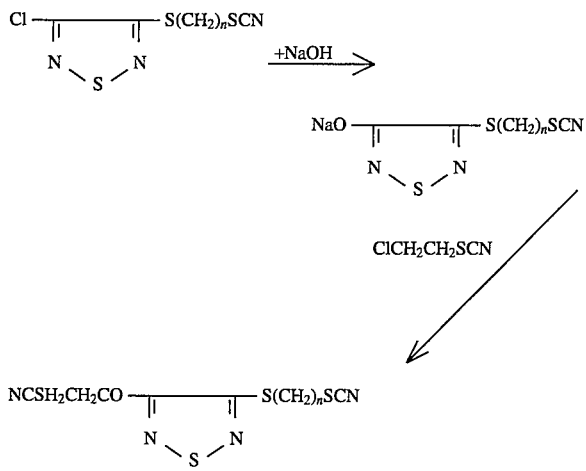

wherein n is as hereinbefore defined.

Preparation of Starting Materials

Chloromethylthiocyanate is well known and is described in JP-B-62215561 and JP-B-62215562.

3,4-Dichloro-1,2,5-thiadiazole is described in U.S. Pat. No. 3,115,497.

The synthesis of cyanogen bromide is described in *Organic Synthesis Collective*, Vol. 2, page 150.

The following examples illustrate the present invention and the manner by which it can be practiced but, as such, should not be construed as limitations upon the overall scope of the same.

Since the hereinabove and hereinafter set forth compound preparation procedures employ only standard chemistry practices and it is known that slightly different reactants can require slightly different reaction parameters from those for other reactants, it is to be understood that minor modifications to the reaction parameters set forth such as the use of an excess of one reactant, the use of a catalyst, the use of high temperature and/or high pressure equipment, high speed mixing and other such conventional changes are within the scope of the present invention.

The desired product can be separated from the reaction product of the above preparative procedures employing conventional separatory procedures known to those skilled in the art including steps of solvent extraction, filtration, water washing, column chromatography, neutralization, acidification, crystallization and distillation.

The structure identity of all compounds is confirmed by proton nuclear magnetic resonance spectroscopy ($^1$H NMR), recorded at 300 MHz; carbon nuclear magnetic resonance spectroscopy ($^{13}$C NMR) recorded at 75 MHz; infrared spectroscopy (IR) and gas chromatography/mass spectrometry (GC/MS). All of the present reactions were conducted at room temperature in a 70 percent ethanol/30 percent water reaction medium unless otherwise stated and under a positive pressure of nitrogen.

EXAMPLE 1

Preparation of 4-Chloro-3-thiocyanato-1,2,5-thiadiazole

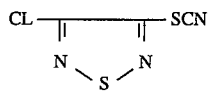

A solution of sodium sulfide (3.43 grams (g), 0.044 mole) in 70 percent ethanol/30 percent water (75 mL) was treated at room temperature with 4,5-dichloro-1,2,5-thiadiazole (6.20 g, 0.04 mole). After stirring for 1 hour, the solution was concentrated to dryness and extracted with ethanol (2 extractions of 30 mL each). Removal of ethanol under reduced pressure gave the sodium salt of the 4-chloro-3-mercapto-1,2,5-thiadiazole. The sodium salt was dispersed in dimethylformamide (15 mL) treated with cyanogen bromide (6.36 g, 0.06 mole) and stirred overnight. The reaction mixture was diluted with water and extracted with methylene chloride. The organic layer was washed with water (3 washings of 40 mL each), dried and concentrated. The residue was chromatographed over silica gel with hexane and ethyl acetate as eluent to yield the 4-chloro-3-thiocyanato-1,2,5-thiadiazole as a yellow solid melting at 63°–65° C. in a yield of 2.5 g, (35 percent of theoretical).

EXAMPLE 2

Preparation of Bis(thiocyanato)-1,2,5-thiadiazole

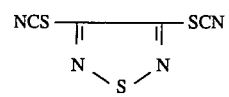

A solution of sodium sulfide (3.12 g, 0.04 mole) in 70 percent ethanol/30 percent water (75 mL) is treated with 4,5-dichloro-1,2,5-thiadiazole (3.10 g, 0.02 mole). After stirring for 1 hour the solution is concentrated to dryness and extracted with ethanol (2 extractions of 30 mL each). Removal of ethanol under reduced pressure gives the disodium salt of the bis(mercapto)-1,2,5-thiadiazole. The disodium salt is dispersed in dimethylformamide (15 mL) and treated with cyanogen bromide (4.32 g, 0.04 mole) and stirred overnight. The reaction mixture is diluted with water and extracted with methylene chloride. The organic layer is washed with water (3 washings of 40 mL each), dried and concentrated. The residue is chromatographed over silica gel with methylene chloride as eluent to yield the bis(thiocyanato)-1,2,5-thiadiazole as an oil (1.4 g, 35 percent of theoretical).

EXAMPLE 3

Preparation of 4-chloro-3-thiomethylthiocyanato-1,2,5,-thiadiazole

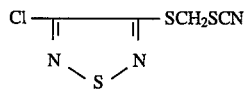

A solution of sodium sulfide (3.43 g, 0.044 mole) in 70 percent ethanol/30 percent water (75 mL) is treated with 4,5-dichloro-1,2,5-thiadiazole (6.20 g, 0.04 mole). After stirring for 1 hour the solution is treated with chloromethyl thiocyanate (6.48 g, 0.06 mole) and stirred overnight. The reaction mixture is concentrated and extracted with methylene chloride. The organic layer is washed with water (3 washings of 40 mL each), dried and concentrated. The residue is chromatographed over silica gel with hexane and ethyl acetate as eluent to yield the 4-chloro-3-thiomethylthiocyanato-1,2,5-thiadiazole as an oil (3.12 g, 35 percent of theoretical).

EXAMPLE 4

Preparation of Bis(thiomethylthiocyanato)-1,2,5-thiadiazole

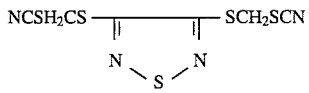

A solution of sodium sulfide (3.12 g, 0.04 mole) in 70 percent ethanol/30 percent water (75 mL) is treated with 4,5-dichloro-1,2,5-thiadiazole (3.10 g, 0.02 mole). After stirring for 1 hour the solution is concentrated to dryness and extracted with ethanol (2 extractions of 30 mL each). Removal of ethanol under reduced pressure gives the disodium salt of the bis(mercapto)-1,2,5-thiadiazole. The disodium salt is dispersed in dimethylformamide (15 mL) and treated with chloromethyl thiocyanate (4.32 g, 0.04 mole) and stirred overnight. The reaction mixture is diluted with water and extracted with methylene chloride. The organic layer is washed with water (3 washings of 40 mL each), dried and concentrated. The residue is chromatographed over silica gel with methylene chloride as eluent to yield the bis(thiomethylthiocyanato)-1,2,5-thiadiazole as an oil (1.86 g, 32 percent of theoretical).

EXAMPLE 5

Preparation of Bis(thioethylthiocyanato)-1,2,5-thiadiazole

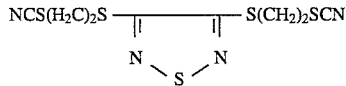

A solution of sodium sulfide (4.42 g, 0.057 mole) in 70 percent ethanol/30 percent water 25 mL) is treated with 4,5-dichloro-1,2,5-thiadiazole (4 g, 0.026 mole). After stirring for 2 hours the solution is concentrated to dryness and extracted with ethanol (2 extractions of 25 mL each). Removal of ethanol under reduced pressure gives the disodium salt of the bis(mercapto)-1,2,5-thiadiazole. The disodium salt is dispersed in dimethylformamide (30 mL) and treated with chloroethyl thiocyanate (6.4 g, 0.0525 mole) and stirred overnight. The reaction mixture is diluted with water and extracted with methylene chloride. The organic layer is washed with water (3 washings of 40 mL each), dried and concentrated. The residue is chromatographed over silica gel with hexane and ethyl acetate as eluent to yield 3.5 g, (42 percent of theoretical) of 3,4-bis(thioethyithiocyanato)-1,2,5-thiadiazole as a yellow solid melting at 72°–74° C.

EXAMPLE 6

Preparation of 4-Chloro-3-thiocyanato-methyloxo-1,2,5-thiadiazole

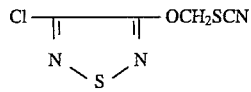

A solution comprised of 5 g of 60 percent pure 4-chloro-3-methoxy-1,2,5-thiadiazole in 30 mL of carbon tetrachloride was irradiated over a period of 45 minutes at 80° C. with a sunlamp while adding a solution comprised of 5 g of sulfuryl chloride in 20 mL of carbon tetrachloride. The reaction mixture was then washed with 30 mL of a saturated aqueous sodium bicarbonate solution and concentrated under reduced pressure to yield 4.87 grams of 4-chloro-3-chloromethoxy-1,2,5-thiadiazole.

The 4-chloro-3-chloromethoxy-1,2,5-thiadiazole (4.87 g) was dissolved in 100 mL of acetone containing a 1.2 equivalent excess of potassium thiocyanate and refluxed overnight (about 16 hours). The reaction mixture was filtered, and concentrated under reduced pressure and the residue chromatographed over silica gel with hexane/ethyl acetate as eluent. The desired 4-chloro-3-thiocyanatomethyloxo-1,2,5-thiadiazole was recovered as an oil in a yield of 37 percent of theoretical. $^1$H NMR (CDCl$_3$) $\delta$5.85 (s, 2H); $^{13}$C NMR (CDCl$_3$) $\delta$72.76, 109.78, 133.51, 156.67; MS (EI) m/e 273, 236, 209, 179, 149, 130.

EXAMPLE 7

Preparation of 4-Methoxy-3-thiocyanato-methyloxo-1,2,5-thiadiazole

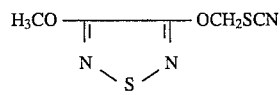

This compound was prepared following the preparative procedures of Example 6 employing 3,4-dimethoxy-1,2,5-thiadiazole as a starting material. The product was recovered as an oil in a yield of 29 percent of theoretical. $^1$H NMR (CDCl$_3$) $\delta$4.16 (s, 3H), 5.85 (s, 2H); $^{13}$C NMR (CDCl$_3$) $\delta$57.94, 72.56, 110.57, 148.43, 152.33; MS (EI) m/e 203(M$^+$), 145, 130, 90, 72.

EXAMPLE 8

Preparation of 3,4-Bis(thiocyanato-methyloxo)-1,2,5-thiadiazole

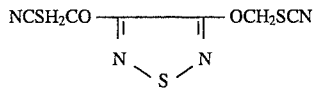

This compound was prepared following the preparative procedures of Example 6 employing 3,4-dimethoxy-1,2,5-thiadiazole as a starting material. The product was recovered in a yield of 16 percent of theoretical as a light yellow solid melting at 74°–75° C. $^1$H NMR (CDCl$_3$) $\delta$5.85 (s, 2H); $^{13}$C NMR (CDCl$_3$) $\delta$72.38, 110.03, 148.42; MS (EI) m/e 203(M$^+$), 260, 202, 130, 102, 100, 72.

Antimicrobial Activity

The compounds of this invention are useful as antimicrobial additives, and they can be added to industrial products such as paints, inks, adhesives, soaps, cutting oils, textiles, paper pigment slurries and styrene-butadiene latexes used for paper coatings to provide needed antimicrobial properties. The compounds are also used as antimicrobial additives in such personal care products as hand creams, lotions, shampoos and hand soaps. A further advantage in the use of the compounds of this invention is their cost-effectiveness for applications which need to have an antimicrobial continuously replenished, such as in cooling towers and pulp and paper mills.

As appreciated by those skilled in the art, each of the compounds disclosed herein are not necessarily active at the same concentrations or against the same microbial species. There may be some compound-to-compound variation in antimicrobial potency and spectrum of antimicrobial activity.

The antimicrobial compounds of the present invention may be added to formulations susceptible to microbial growth. They may be added either undiluted or dissolved in inert diluents such as organic solvents such as glycols, alcohols or acetone. They may also be added alone or in combination with other preservatives.

As used herein, the term "microorganism" is meant to refer to bacteria, fungi, viruses, algae, subviral agents and protozoa.

As used herein, the term "antimicrobially-effective amount" refers to that amount of one or a mixture of the compounds, or of a composition comprising such compound or compounds, of this invention needed to exhibit inhibition of selected microorganisms. Typically, this amount varies from providing about 1 part per million (ppm) to about 5,000 ppm by weight of the compound to a microbial habitat being contacted with the compound. Such amounts typically vary depending upon the particular compound tested and microorganism treated. Additionally, the exact concentration of the compounds to be added in the treatment of industrial and consumer formulations may vary within a product type depending upon the components of the formulation. A preferred effective amount of the compound is from about 1 ppm to about 500 ppm, more preferably from about 1 ppm to about 50 ppm by weighty of a microbial habitat.

The term "habitat" refers to a place or site where a microorganism naturally or normally lives or grows. Typically, such a habitat will be an area that provides a moisture source, nutrient source, and/or an oxygen source such as, for example, a cooling water tower or an air washing system.

The terms "inhibition", "inhibit" or "inhibiting" refer to the suppression, stasis, kill, or any other interference with the normal life processes of microorganisms that is adverse to such microorganisms, so as to destroy or irreversibly inactivate existing microorganisms and/or prevent or control their future growth and reproduction.

The antimicrobial activity of the compounds of the present invention is demonstrated by the following techniques.

TABLE I

Identification of Compounds Used in Antimicrobial Activity Tests

| Compound Example No. | Chemical Identity |
|---|---|
| 1 | 4-Chloro-3-thiocyanato-1,2,5-thiadiazole |
| 2 | Bis(thiocyanato)-1,2,5-thiadiazole |
| 3 | 4-Chloro-3-thiomethylthiocyanato-1,2,5-thiadiazole |
| 4 | Bis(thiomethylthiocyanato)-1,2,5-thiadiazole |
| 5 | Bis(thioethylthiocyanato)-1,2,5-thiadiazole |
| 6 | 4-Chloro-3-thiocyanamethyloxo-1,2,5-thiadiazole |
| 7 | 4-Methoxy-3-thiocyanomethyloxo-1,2,5-thiadiazole |
| 8 | Bis(thiocyanomethyloxo)-1,2,5-thiadiazole |

The minimum inhibitory concentration (MIC) for the compounds listed in Table I is determined for bacteria, using nutrient agar, and 7 yeast and fungi, using malt yeast agar. A one percent solution of the test compound is prepared in a mixture of acetone and water.

Nutrient agar is prepared at pH 6.8, representing a neutral medium, and at pH 8.2, representing an alkaline medium. The nutrient agars are prepared by adding 23 g of nutrient agar to one-liter of deionized water. In addition, the alkaline medium is prepared by adjusting a 0.04M solution of N-(tris-(hydroxymethyl)methyl)glycine buffered deionized water with concentrated sodium hydroxide to a pH of 8.5.

Malt yeast agar is prepared by adding 3 g yeast extract and 45 g malt agar per liter of deionized water. The specific agar is dispensed in 30 mL aliquots into 25×200 mm test tubes, capped and autoclaved for 15 minutes at 115° C.

The test tubes containing the agar are cooled in a water bath until the temperature of the agar is 48° C. Then, an appropriate amount of the one percent solution of the test compound is added (except in the controls where no compound is added) to the respective test tubes so that the final concentrations are 500, 250, 100, 50, 25, 10, 2.5, 1.0 and zero parts per million of the test compound in the agar, thus having a known concentration of test compound dispersed therein. The contents of the test tubes are then transferred to respective petri plates. After drying for 24 hours, the petri plates containing nutrient agar are inoculated with bacteria and those containing malt yeast agar are inoculated with yeast and fungi.

The inoculation with bacteria is accomplished by using the following procedure. Twenty-four hour-cultures of each of the bacteria are prepared by incubating the respective bacteria in tubes containing nutrient broth for 24 hours at 30° C. in a shaker. Dilutions of each of the 24 hour-cultures are made so that nine separate suspensions (one for each of the nine test bacteria) are made, each containing $10^8$ colony forming units (CFU) per mL of suspension of a particular bacteria. Aliquots of 0.3 mL of each of the bacterial suspensions are used to fill the individual wells of Steer's Replicator. For each microbial suspension, 0.3 mL was used to fill three wells (i.e., three wells of 0.3 mL each) so that for the nine different bacteria, 27 wells are filled. The Steer's Replicator is then used to inoculate both the neutral and alkaline pH nutrient agar petri plates.

The inoculated petri plates are incubated at 30° C. for 48 hours and then read to determine if the test compound which is incorporated into the agar prevented growth of the respective bacteria.

The inoculation with the yeast and fungi is accomplished as follows. Cultures of yeast and fungi are incubated for seven days on malt yeast agar at 30° C. These cultures are used to prepare suspensions by the following procedure. A suspension of each organism is prepared by adding 10 mL of sterile saline and 10 microliters of octylphenoxy polyethoxy ethanol to the agar slant of yeast or fungi. The sterile saline/octylphenoxy polyethoxy ethanol solution is then agitated with a sterile swab to suspend the microorganism grown on the slant. Each resulting suspension is diluted into sterile saline (1 part suspension: 9 parts sterile saline). Aliquots of these dilutions are placed in individual wells of Steer's Replicator and petri plates inoculated as previously described. The petri plates are incubated at 30° C. and read after 48 hours for yeast and 72 hours for fungi.

Table II lists the bacteria, yeast and fungi used in the MIC test described above along with their respective American Type Culture Collection (ATCC) identification numbers.

TABLE II

Organisms Used in the Minimum Inhibitory Concentration Test

| Organism | ATCC No. |
|---|---|
| Bacteria | |
| *Bacillus subtilis* (Bs) | 8473 |
| *Enterobacter aerogenes* (Ea) | 13048 |
| *Escherichia coli* (Ec) | 11229 |
| *Klebsiella pneumonias* (Kp) | 8308 |
| *Proteus vulgaris* (Pv) | 881 |
| *Pseudomonas aeruginosa* (Pa) | 10145 |
| *Pseudomonas aeruginosa* (PRD-10) | 15442 |
| *Salmonella choleraesuis* (Sc) | 10708 |
| *Staphylococcus aureus* (Sa) | 6538 |
| Yeast/Fungi | |
| *Aspergillus niger* (An) | 16404 |
| *Candida albicans* (Ca) | 10231 |
| *Penicillium chrysogenum* (Pc) | 9480 |
| *Saccharomyces cerevisiae* (Sc) | 4105 |
| *Trichoderma viride* (Tv) | 8678 |
| *Aureobasidium pullulan* (Ap) | 16622 |
| *Fusarium oxysporum* (Fo) | 48112 |

In Tables III and IV, the MIC values of the compounds described in Table I as compared to the MIC of a standard commercial preservative (with 1-(3-chloroalkyl)-3,5,7-triaza-1-azoniaadamantane chloride as the active agent and referred to in Tables III and IV as "STANDARD I") are set forth for the bacteria organisms and yeast/fungi organisms which are listed in Table II.

TABLE III

Minimum Inhibitory Concentrations for Test Compounds in Bacteria Species (in ppm)

| Compound Example No. | Bs | Ea | Ec | Kp | Pv | PRD | Pa | Sc | Sa |
|---|---|---|---|---|---|---|---|---|---|
| STANDARD I | | | | | | | | | |
| pH 6.8 | 50 | 100 | 100 | 50 | 50 | 100 | 100 | 50 | 100 |
| pH 8.2 | 250 | 250 | 250 | 250 | 250 | 500 | >500 | 100 | 250 |
| (1) pH 6.8 | 25 | 50 | 25 | 25 | 25 | 50 | 25 | 25 | 25 |
| pH 8.2 | 500 | >500 | >500 | >500 | >500 | >500 | >500 | >500 | >500 |
| (2) pH 6.8 | 25 | 25 | 25 | 25 | 25 | 25 | 50 | 25 | 25 |
| pH 8.2 | 100 | 100 | 50 | 250 | 100 | 250 | 250 | 100 | 100 |
| (3) pH 6.8 | <10 | 25 | 25 | 25 | <10 | <10 | 25 | 25 | 25 |
| pH 8.2 | 25 | 100 | 50 | 50 | 25 | 25 | 100 | 50 | 50 |
| (4) pH 6.8 | <10 | 25 | 25 | <10 | <10 | 25 | <10 | 25 | <10 |
| pH 8.2 | <10 | <10 | <10 | <10 | <10 | 25 | <10 | 25 | <10 |
| (5) pH 6.8 | >500 | >500 | >500 | >500 | >500 | >500 | >500 | >500 | >500 |
| pH 8.2 | >500 | >500 | >500 | >500 | >500 | >500 | >500 | >500 | >500 |
| (6) pH 6.8 | <10 | 50 | 25 | 25 | <10 | 100 | 50 | <10 | 25 |
| pH 8.2 | 25 | 50 | 25 | 25 | 25 | 100 | 50 | 25 | 25 |
| (7) pH 6.8 | <10 | 25 | 25 | <10 | <10 | 25 | <10 | 25 | <10 |
| pH 8.2 | — | — | — | — | — | — | — | — | — |
| (8) pH 6.8 | <10 | 250 | 50 | 100 | 25 | 500 | 250 | 25 | 25 |
| pH 8.2 | 25 | 250 | 100 | 50 | 25 | 250 | 100 | 50 | 25 |

TABLE IV

Minimum Inhibitory Concentrations for Test Compounds in Yeast/Fungi Species (in ppm)

| COMPOUND | An | Ca | Pc | Sc | Tv | Ap | Fo |
|---|---|---|---|---|---|---|---|
| STANDARD I | >500 | >500 | >500 | 500 | >500 | >500 | >500 |
| 1 | <10 | <10 | <10 | <10 | <10 | <10 | <10 |
| 2 | <1 | <1 | <1 | 5 | 5 | <1 | 2.5 |
| 3 | <10 | <10 | <10 | <10 | <10 | <10 | <10 |
| 4 | <2.5 | <2.5 | <2.5 | <2.5 | 10 | <2.5 | <2.5 |
| 5 | <10 | 100 | <10 | <10 | >500 | <10 | 250 |
| 6 | <10 | <10 | <10 | <10 | 25 | <10 | <10 |
| 7 | <10 | 25 | <10 | <10 | 25 | <10 | <10 |
| 8 | <10 | 50 | <10 | 25 | 50 | <10 | 25 |

Marine Antifouling Activity

The present invention is also directed to a method for inhibiting marine organisms. The term "marine organisms" is meant to include marine animals, such as barnacles, serpulid, bryozoa, oysters and hydroids, and marine plants, such as green algae and brown algae. The method for inhibiting marine organisms comprises contacting a surface exposed to a marine environment in which marine organisms grow with a marine antifouling effective amount of the compound of this invention.

As appreciated by those skilled in the art, not all of the compounds disclosed herein are active at the same concentrations or against the same marine organism species. That is, there may be some compound-to-compound variation in marine antifouling potency and spectrum of marine antifouling activity. Furthermore, a compound's marine antifouling activity may be dependent on the specific materials with which the compound is formulated to form a marine antifouling composition.

As used herein, the term "marine antifouling effective amount" refers to that amount of one or a mixture of two or more of the compounds of this invention needed to exhibit inhibition of selected marine organisms. Typically, this amount varies from providing about 1 weight percent to about 30 weight percent of the compound to a marine antifouling composition which is used to treat a surface exposed to a marine environment in which marine organisms live or grow. Such amounts vary depending upon the particular compound tested and marine organism to be treated. Also, the exact concentration of the compounds to be added in the preparation of industrial and consumer formulations may vary within a product type depending upon the components of the formulation.

A composition comprising a marine antifouling effective amount of the compound will also comprise an inert diluent which may be, for example, in the form of a paint. Particularly preferred are those paints having a vinyl resin binder such as, for example, a plasticized polyvinyl chloride or a polyvinyl chloride-polyvinyl acetate type. Preferably, the binders are formulated as latexes or emulsions. In a paint composition, the compound of the present invention is preferably used in an amount from about 1 to about 30 weight percent and, most preferably, from about 10 to about 25 weight percent. In addition to vinyl resin binder paints, epoxy and polyurethane binder paints containing the compound may also be useful. Coatings and films prepared from paints comprising the compound of the present invention typically remain substantially free from build-up of marine organisms for periods ranging from about 3 to about 12 months, depending upon the concentration of the compound and the thickness of the applied coating or film.

The term "a surface exposed to a marine environment" refers to a surface where a marine organism naturally or normally lives or grows. Typically, such a surface will be an area that is in continual or periodic contact with a marine environment such as an ocean or other body of water. Typical surfaces include, for example, a ship hull.

The marine antifouling activity of the compounds of the present invention is demonstrated by the following techniques.

Test panels are prepared from clear, rigid polyvinyl chloride film that is $0.381 \times 10^{-3}$ m thick and has one textured surface. The test panels are 0.1524 m by 0.1524 m squares that have 0.00635 m holes punched at corners on 0.127 m centers. A 0.102 square template, with a 0.067 m diameter hole at the center, is attached to the center of the textured surface of the test panels.

A candidate marine antifoulant compound (1.0 g) is stirred into a resinous latex binder (9.0 g). A portion of the compound/binder mixture (1.5 g, is added to the center of the test panel and uniformly spread over the circular area inside the template.

Water is added dropwise as needed to properly spread the compound/binder mixture. The template prevents the compound/binder mixture from spreading beyond the uncovered area. The test panel is allowed to sit for between 10 to 30 minutes until the edge of the spread compound/binder mixture has dried. The template is then removed. The test panel is then allowed to dry for 8 to 12 hours at room temperature.

Two test panels are prepared for each candidate marine antifoulant compound. Two control test panels are also prepared by only treating with the resinous latex binder. One test panel of each candidate marine surfactant compound is attached over a white background to the topside of an exposure support apparatus. The second test panel is attached over a black background to the underside of the exposure support apparatus. The exposure support apparatus is placed horizontally 0.0254 m under a marine surface with the white background topside facing up. The exposure support apparatus is exposed to the marine environment for both 3 and 6 weeks during which time the control test panels become substantially covered with mature marine organism growth on both the topside and underside exposures.

After being removed from the exposure support apparatus, each test panel is inspected and rated for marine organism growth on both the treated and untreated areas of the test panel. The marine organisms present on the treated and untreated areas are noted. The presence of algae spores and bacterial slime are noted but not included in rating each test panel. The test panels are rated on a scale from 10 (representing completely free of marine organism growth) to 0 (representing completely covered with marine organism growth).

In Table V, the marine antifouling rating values for some of the compounds listed in Table I are set forth, as well as the ratings for control panels (with no marine antifouling compound and referred to in Table V as "Control").

In addition, test panels were prepared using tributyl tin oxide, a known marine antifouling compound. One set of such panels used the tributyl tin oxide in a commercially available ship-hull paint (referred to in Table V as "STANDARD II") which was employed in the same manner as the resinous latex binder used on the other test panels. A second set of such panels used the tributyl tin oxide at a 10 percent concentration in the resinous latex binder (referred to in Table V as "STANDARD III").

TABLE V

Marine Antifouling Rating for Test Compounds

| Compound Example No. | Marine Antifouling Ratings | | | |
| --- | --- | --- | --- | --- |
| | 10 Week Test | | 20 Week Test | |
| | Top Panel | Bottom Panel | Top Panel | Bottom Panel |
| 2 | 9 | 9 | 2 | 7 |
| 4 | 9 | 9 | 7 | 5 |
| Control | 7 | 1 | 1 | 1 |
| STANDARD II | 10 | 7 | 9 | 7 |
| STANDARD III | 9 | 8 | 9 | 7 |

What is claimed is:

1. A compound corresponding to the formula $$X \underset{N \diagdown S \diagup N}{\overset{\|\quad\quad\|}{\boxed{\phantom{XXXX}}}} Y$$

wherein X and Y independently represent —Br, —Cl, —OCH$_3$, —SCN, —OCH$_2$SCN, —SCH$_2$SCN, —OCH$_2$CH$_2$SCN or —SCH$_2$CH$_2$SCN, provided that at least one of X or Y represents —SCN, —OCH$_2$SCN, —SCH$_2$SCN, —OCH$_2$CH$_2$SCN or —SCH$_2$CH$_2$SCN.

2. A compound of claim 1 wherein X represents —Cl or —SCN when Y represents —SCN.

3. The compound of claim 2 which is 4-chloro-3-thiocyanato-1,2,5-thiadiazole.

4. The compound of claim 2 which is bis(thiocyanato)-1,2,5-thiadiazole.

5. A compound of claim 1 wherein X represents —Cl or —SCH$_2$SCN when Y represents —SCH$_2$SCN.

6. The compound of claim 5 which is 4-chloro-3-thiomethylthiocyanato-1,2,5-thiadiazole.

7. The compound of claim 5 which is bis(thiomethylthiocyanato)-1,2,5-thiadiazole.

8. A compound of claim 1 wherein X represents —Cl or —SCH$_2$CH$_2$SCN when Y represents —SCH$_2$CH$_2$SCN.

9. The compound of claim 8 which is bis(thioethylthiocyanato)-1,2,5-thiadiazole.

10. A compound of claim 1 wherein X represents —Cl, —OCH$_3$, or —OCH$_2$SCN when Y represents —OCH$_2$SCN.

11. The compound of claim 10 which is 4-chloro-3-thiocyanatomethyloxo-1,2,5-thiadiazole.

12. The compound of claim 10 which is 4-methoxy-3-thiocyanatomethyloxo-1,2,5-thiadiazole.

13. The compound of claim 10 which is bis(thiocyanatomethyloxo)-1,2,5-thiadiazole.

14. An antimicrobial composition comprising an inert diluent and an antimicrobially-effective amount of a compound corresponding to the formula:

$$X \underset{N \diagdown S \diagup N}{\overset{\|\quad\quad\|}{\boxed{\phantom{XXXX}}}} Y$$

wherein X and Y independently represent —Br, —Cl, —OCH$_3$, —SCN, —OCH$_2$SCN, —SCH$_2$SCN, —OCH$_2$CH$_2$SCN or —SCH$_2$CH$_2$SCN, provided that at least one of X or Y represents —SCN, —OCH$_2$SCN, —SCH$_2$SCN, —OCH$_2$CH$_2$SCN or —SCH$_2$CH$_2$SCN.

15. A composition of claim 14 wherein X represents —Cl or —SCN when Y represents —SCN.

16. The composition of claim 15 wherein the compound is 4-chloro-3-thiocyanato-1,2,5-thiadiazole.

17. The composition of claim 15 wherein the compound is bis(thiocyanato)-1,2,5-thiadiazole.

18. A composition of claim 14 wherein X represents —Cl or —SCH$_2$SCN when Y represents —SCH$_2$SCN.

19. The composition of claim 18 wherein the compound is 4-chloro-3-thiomethylthiocyanato-1,2,5-thiadiazole.

20. The composition of claim 18 wherein the compound is bis(thiomethylthiocyanato)-1,2,5-thiadiazole.

21. A composition of claim 14 wherein X represents —Cl or —SCH$_2$CH$_2$SCN when Y represents —SCH$_2$CH$_2$SCN.

22. The composition of claim 21 wherein the compound is bis(thioethylthiocyanato)-1,2,5-thiadiazole.

23. A composition of claim 14 wherein X represents —Cl, —OCH$_3$, or —OCH$_2$SCN when Y represents —OCH$_2$SCN.

24. The composition of claim 23 wherein the compound is 4-chloro-3-thiocyanatomethyloxo-1,2,5-thiadiazole.

25. The composition of claim 23 wherein the compound is 4-methoxy-3-thiocyanatomethyloxo-1,2,5-thiadiazole.

26. The composition of claim 23 wherein the compound is bis(thiocyanatomethyloxo)-1,2,5-thiadiazole.

27. The composition of claim 14 wherein the compound is present in an amount to provide from about 1 part per million to about 5,000 parts per million by weight of the compound to a microbial habitat that is contacted with the composition.

28. A method for inhibiting microorganisms in a microbial habitat comprising contacting said microbial habitat with an antimicrobially-effective amount of a compound corresponding to the formula:

$$X \underset{N \diagdown S \diagup N}{\overset{\|\quad\quad\|}{\boxed{\phantom{XXXX}}}} Y$$

wherein X and Y independently represent —Br, —Cl, —OCH$_3$, —SCN, —OCH$_2$SCN, —SCH$_2$SCN, —OCH$_2$CH$_2$SCN or —SCH$_2$CH$_2$SCN, provided that at least one of X or Y represents —SCN, —OCH$_2$SCN, —SCH$_2$SCN, —OCH$_2$CH$_2$SCN or —SCH$_2$CH$_2$SCN.

29. A method of claim 28 wherein X represents —Cl or —SCN when Y represents —SCN.

30. The method of claim 29 wherein the compound is 4-chloro-3-thiocyanato-1,2,5-thiadiazole.

31. The method of claim 29 wherein the compound is bis(thiocyanato)-1,2,5-thiadiazole.

32. A method of claim 28 wherein X represents —Cl or —SCH$_2$SCN when Y represents —SCH$_2$SCN.

33. The method of claim 32 wherein the compound is 4-chloro-3-thiomethylthiocyanato-1,2,5-thiadiazole.

34. The method of claim 32 wherein the compound is bis(thiomethylthiocyanato)-1,2,5-thiadiazole.

35. A method of claim 28 wherein X represents —Cl or —SCH$_2$CH$_2$SCN when Y represents —SCH$_2$CH$_2$SCN.

36. The method of claim 35 wherein the compound is bis(thioethylthiocyanato)-1,2,5-thiadiazole.

37. A method of claim 28 wherein X represents —Cl, —OCH$_3$, or —OCH$_2$SCN when Y represents —OCH$_2$SCN.

38. The method of claim 37 wherein the compound is 4-chloro-3-thiocyanatomethyloxo-1,2,5-thiadiazole.

39. The method of claim 37 wherein the compound is 4-methoxy-3-thiocyanatomethyloxo-1,2,5-thiadiazole.

40. The method of claim 37 wherein the compound is bis(thiocyanatomethyloxo)-1,2,5-thiadiazole.

41. The method of claim 28 wherein the compound is present in an amount to provide from about 1 part per million to about 5,000 parts per million by weight of the compound to a microbial habitat that is contacted with the composition.

42. A composition useful in preventing the growth of marine organisms on a surface exposed to a marine environment in which marine organisms grow comprising an inert diluent and a marine antifouling effective amount of a compound corresponding to the formula:

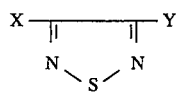

wherein X and Y independently represent —Br, —Cl, —OCH$_3$, —SCN, —OCH$_2$SCN, —SCH$_2$SCN, —OCH$_2$CH$_2$SCN or —SCH$_2$CH$_2$SCN, provided that at least one of X or Y represents —SCN, —OCH$_2$SCN, —SCH$_2$SCN, —OCH$_2$CH$_2$SCN or —SCH$_2$CH$_2$SCN.

43. The composition of claim 42 wherein the compound is present in the composition in an amount from about 1 weight percent to about 30 weight percent.

44. A method for preventing the growth of marine organisms on a surface exposed to a marine environment in which marine organisms grow comprising contacting said surface with a marine antifouling effective amount of a compound corresponding to the formula:

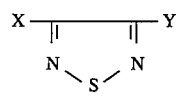

wherein X and Y independently represent —Br, —Cl, —OCH$_3$, —SCN, —OCH$_2$SCN, —SCH$_2$SCN, —OCH$_2$CH$_2$SCN or —SCH$_2$CH$_2$SCN, provided that at least one of X or Y represents —SCN, —OCH$_2$SCN, —SCH$_2$SCN, —OCH$_2$CH$_2$SCN or —SCH$_2$CH$_2$SCN.

45. The method of claim 44 wherein the compound is contacted with the surface in an amount from about 1 to about 30 weight percent of a composition comprising an inert diluent and the compound.

* * * * *